US009277927B2

(12) United States Patent
Khanna et al.

(10) Patent No.: US 9,277,927 B2
(45) Date of Patent: Mar. 8, 2016

(54) MINIMALLY-INVASIVE DEVICE, KIT, AND METHOD FOR HARVESTING BONE GRAFT

(75) Inventors: Akhil Jay Khanna, Baltimore, MD (US); Peter Hwa-Ming Truskey, Baltimore, MD (US); Maxim Budyansky, Baltimore, MD (US); Shoval Dekel, Baltimore, MD (US); Haim Gottfried, Baltimore, MD (US); Neil Shah, Baltimore, MD (US); Khaled M. Kebaish, Baltimore, MD (US); Lee Hunter Riley, III, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 288 days.

(21) Appl. No.: 13/984,247

(22) PCT Filed: Feb. 10, 2012

(86) PCT No.: PCT/US2012/024761
§ 371 (c)(1),
(2), (4) Date: Aug. 7, 2013

(87) PCT Pub. No.: WO2012/109620
PCT Pub. Date: Aug. 16, 2012

(65) Prior Publication Data
US 2013/0317507 A1    Nov. 28, 2013
US 2014/0188115 A9    Jul. 3, 2014

Related U.S. Application Data

(60) Provisional application No. 61/441,955, filed on Feb. 1, 2011, provisional application No. 61/471,273, filed on Apr. 4, 2011.

(51) Int. Cl.
*A61B 17/00* (2006.01)
*A61B 17/16* (2006.01)

(52) U.S. Cl.
CPC .................. *A61B 17/1635* (2013.01)

(58) Field of Classification Search
CPC combination set(s) only.
See application file for complete search history.

(56) References Cited

U.S. PATENT DOCUMENTS

| 8,118,813 | B2* | 2/2012 | Perez-Cruet ....... A61B 17/1671 606/93 |
|---|---|---|---|
| 2002/0058945 | A1 | 5/2002 | Steiner et al. |
| 2007/0055282 | A1 | 3/2007 | Muschler |
| 2008/0243123 | A1 | 10/2008 | Gordils Wallis et al. |
| 2010/0178631 | A1 | 7/2010 | Gordils Wallis et al. |

OTHER PUBLICATIONS

International Search Report and Written Opinion of PCT/US2012/024761.

* cited by examiner

*Primary Examiner* — Sameh Boles
(74) *Attorney, Agent, or Firm* — Venable LLP; Henry J. Daley

(57) ABSTRACT

A minimally-invasive bone graft harvesting device, kit, and method are provided. The device includes a hollow cutting element and an extraction element. The hollow cutting element may define a longitudinal axis and includes a distal end, a proximal end adapted to be coupled to a powered or manual-operated rotary tool, and an inner lumen extending longitudinally between the distal and proximal ends. The hollow cutting element may also include one or more blades protruding from an outer surface of the cutting element. Each blade may be arranged adjacent to an opening extending between the outer surface and the inner lumen to allow cancellous bone material cut by each blade during use to pass through the opening into the inner lumen. The extraction element may be removably received within the inner lumen of the hollow cutting element to allow withdrawal of the bone material in the inner lumen.

9 Claims, 11 Drawing Sheets

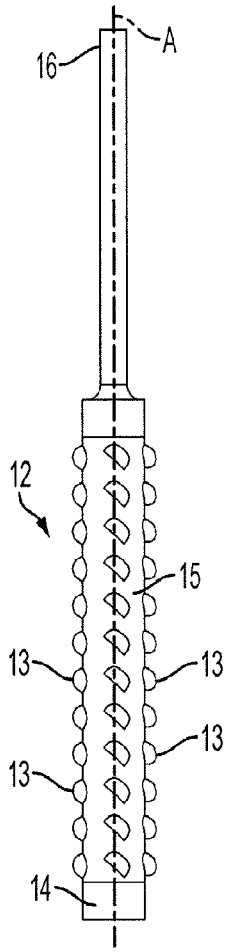
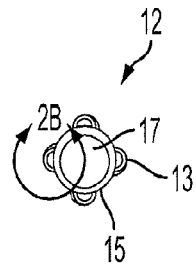
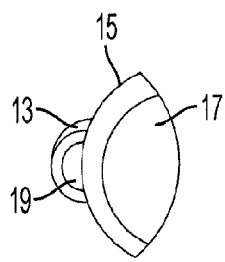
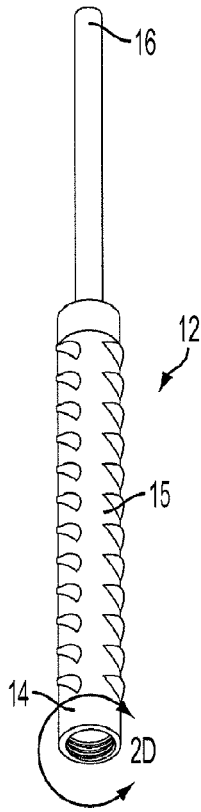
FIG. 2
FIG. 2A
FIG. 2B
FIG. 2C
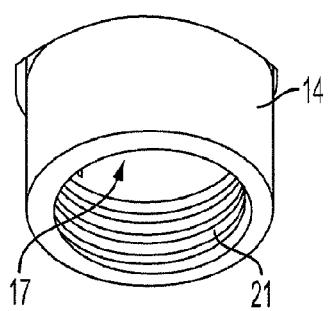
FIG. 2D

MINIMALLY-INVASIVE DEVICE, KIT, AND METHOD FOR HARVESTING BONE GRAFT

CROSS-REFERENCE OF RELATED APPLICATION

This is a national stage application under 35 U.S.C. 371 of PCT/US2012/024761 filed Feb. 10, 2012, the entire contents of which are incorporated herein by reference and that claims priority to U.S. Provisional Application No. 61/441,955 filed Feb. 11, 2011. This application claims priority to U.S. Provisional Application No. 61/471,273, filed Apr. 4, 2011. The entire contents of each of the foregoing applications are hereby incorporated by reference.

BACKGROUND

1. Field of Invention

The field of the currently claimed embodiments of this invention generally relates to devices and methods for harvesting bone grafts.

2. Discussion of Related Art

In the current U.S. healthcare market, cost constraints are becoming a central and ever-growing issue. In this landscape, hospitals and surgeons are being pressured to cut the costs of various procedures while still maintaining good clinical outcomes. One area which has potential to concurrently reduce costs and increase care is in the area of bone graft harvesting for use in complex surgical procedures such as, for example, spinal fusions. Hundreds of thousands of people in the U.S., and millions worldwide, undergo spinal fusion procedures every year. Generally speaking, the long term success of a spinal fusion is dependent on a successful bone graft for inducing the fusion of two spinal vertebrae. A failed fusion can mean an additional surgical procedure, with potentially life threatening risks to the patient, as well as huge additional costs to the healthcare system.

According to at least one common procedure, a bone graft may be harvested from the patient's own body (autologous bone) such as, for example, from the iliac crest, the superior border of the wing of ilium and the superolateral margin of the pelvis. Autologous bone is often preferred because there is less risk of graft rejection since the graft originated from the patient's own body. Nevertheless, there are still risks and substantial costs associated with harvesting bone grafts using currently available techniques and methods.

There is a need for new bone harvesting methods and devices which are complementary to spinal fusion surgeries (as well as other uses of autografts such as, for example, maxiofacial reconstruction, dental procedures, bone trauma, bone cancer, fracture repairs and joint replacement, etc.) and which allow hospitals to maintain high standards of care at a fraction of the cost of current options without compromising patient safety. In particular, there is a need for a minimally-invasive device and method to harvest iliac crest bone graft (ICBG) to help reduce the morbidity associated with bone harvesting procedures and allow physicians to achieve high fusion rates without burdening the hospitals with the high costs of utilizing bone graft substitutes such as bone morphogenetic proteins (BMP) products, allografts, or demineralized bone matrices (DBM).

SUMMARY

According to an embodiment, a minimally-invasive bone graft harvesting device includes a hollow cutting element and an extraction element. The hollow cutting element may define a longitudinal axis and includes a distal end, a proximal end adapted to be coupled to a powered or manual-operated rotary tool, and an inner lumen extending longitudinally between the distal and proximal ends. The hollow cutting element may also include one or more blades protruding from an outer surface of the cutting element. Each blade may be arranged adjacent to an opening extending between the outer surface and the inner lumen to allow cancellous bone material cut by each blade during use to pass through the opening into the inner lumen. The extraction element may be removably received within the inner lumen of the hollow cutting element to allow withdrawal of the bone material in the inner lumen.

According to another embodiment, a kit for minimally-invasive bone graft harvesting may be provided including the aforementioned device, and a tubular access port. The tubular access port may be removably secured to a bone to allow passage of the hollow cutting element therethrough. The access port includes a bone-engaging portion and a flexible tube portion. The bone-engagement portion is provided at a distal end and includes a plurality of teeth for cutting into the bone and a threaded portion for securing the access port to the bone. The flexible tube portion extends from the bone-engaging portion to an opening at a proximal end.

According to another embodiment, a minimally-invasive method for bone graft harvesting comprises inserting the distal end of the cutting element in an axial direction through a hole in a cortical shell of a bone and into a cancellous region to a predetermined depth. The hole may define a fixed point of rotation. The method may further include the step of laterally sweeping the distal end of the cutting element through the cancellous region of the bone in an arc about the fixed point of rotation. During insertion and sweeping, the cutting element is rotated about the longitudinal axis by the rotary tool such that bone material cut by the one ore more blades passes through the adjacent surface openings into the inner lumen of the cutting element.

According to another embodiment, a minimally-invasive bone graft harvesting device comprises a hollow cutting element, an extraction element, and a bone material collection canister. The hollow cutting element may include a distal end having a cutting tip; a proximal end coupled to a powered or manual-operated rotary tool; an inner lumen extending longitudinally between the distal and proximal ends; and at least one opening extending between an outer surface of the cutting element and the inner lumen to allow cancellous bone material to pass through the opening into the inner lumen. The extraction element may be movably received within the inner lumen of the hollow cutting element to allow withdrawal of the bone material in the inner lumen. The extraction element may extend through an opening at the proximal end of the cutting element. The cutting element extends through the bone material collection canister and includes a hole in the outer surface along a portion enclosed within the canister. When the extraction element is moved longitudinally toward the proximal end of the cutting element, bone material disposed within the inner lumen is moved proximally by the distal disk and deposited in the collection canister through the hole in the outer surface of the cutting element.

Further features and advantages, as well as the structure and operation of various example embodiments of the invention, are described in detail below with reference to the accompanying drawings.

BRIEF DESCRIPTION OF THE DRAWINGS

The foregoing and other features and advantages of the invention will be apparent from the following, more particular description of some embodiments of the invention, as illustrated in the accompanying drawings. Unless otherwise indicated, the accompanying drawing figures are not to scale. Several embodiments of the invention will be described with respect to the following drawings, in which like reference numerals represent like features throughout the figures, and in which:

FIG. 2 is a side view of a hollow cutting element of the minimally-invasive device for bone graft harvesting of FIG. 1 according to an embodiment of the invention;

FIG. 2A is a bottom view of the cutting element shown in FIG. 2;

FIG. 2B is a detailed partial bottom view of a blade disposed on an outer surface of the cutting element of FIGS. 2 and 2A;

FIG. 2C is a bottom perspective view of the cutting element of FIG. 2;

FIG. 2D is a detailed bottom view of a distal end of the cutting element of FIG. 2C;

DETAILED DESCRIPTION

Some embodiments of the current invention are discussed in detail below. In describing embodiments, specific terminology is employed for the sake of clarity. However, the invention is not intended to be limited to the specific terminology so selected. A person skilled in the relevant art will recognize that other equivalent components can be employed and other methods developed without departing from the broad concepts of the current invention. All references cited anywhere in this specification, including the Background and Detailed Description sections, are incorporated by reference as if each had been individually incorporated.

Figure 1:
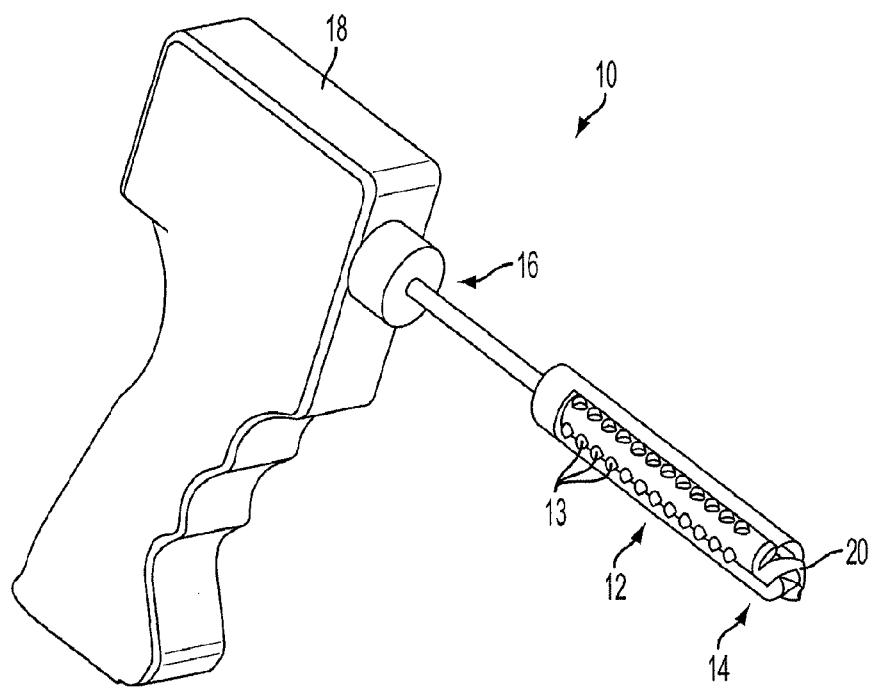
FIG. 1 is a perspective view of a minimally-invasive device for bone graft harvesting according to an embodiment of the invention.
Figure 1A:
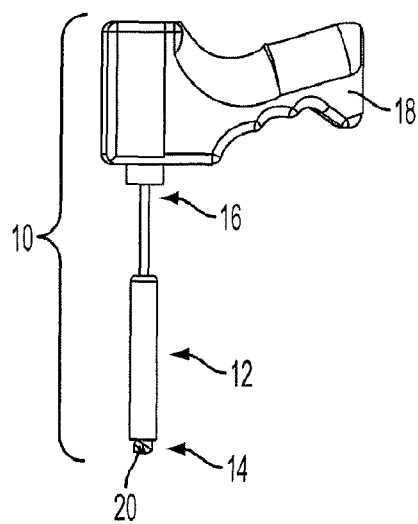
FIG. 1A is a side view of the minimally-invasive device for bone graft harvesting of FIG. 1.

FIGS. 1 and 1A depict perspective and side views, respectively, of a minimally-invasive device 10 for bone graft harvesting according to an embodiment of the invention. The device 10 may include a hollow cutting element 12 having a distal end 14 and a proximal end 16. The proximal end 16 may be coupled to a powered or manually-operable rotary tool 18 such as, for example but not limited to, any currently available or specially designed surgical drill, power saw, or a manually gripped T-handle or knob. The device 10 may include a distal cutting tip 20 arranged at the distal end of the cutting element 12. The cutting tip 20 may be part of the cutting element 12 or, as shown and discussed further below, may be part of an extraction element removably received within the cutting element 12. The cutting element 12 may also include one or more blades 13 protruding from an outer surface of the cutting element 12.

FIG. 2 is a side view of the hollow cutting element 12 according to an embodiment. As shown, the cutting element 12 is substantially cylindrical in cross-section, although other shapes including, for example but not limited to, elliptical, triangular, rectangular, conical, and the like are also envisioned. The blades 13 protrude radially outwardly from the outer surface 15 of the cutting element 12 and have cutting edges canted relative to the longitudinal axis to provide the desired cutting or carving path when the cutting element 12 is axially advanced while rotating about the longitudinal axis A.

Although the blades 13 are shown in FIG. 2 as being provided in four longitudinally arranged rows spaced circumferentially from one another on the outer surface 15 with each row having twelve blades, this is purely for illustration and one of ordinary skill in the art will recognize that more or fewer rows and/or blades 13 may be provided and that the blades 13 may be arranged in any number of other patterns or even randomly on the outer surface 15. FIG. 2A is a detailed bottom view of the cutting element 12 and shows the inner lumen 17. FIG. 2B is a detailed partial bottom view of the cutting element 12 showing one of the blades 13 disposed on the outer surface 15. As can be seen, an opening 19 is arranged adjacent to the blade 13 and extends between the outer surface 15 and the inner lumen 17 of the cutting element 12. In use, the opening 19 allows cancellous bone material cut or morselized by the adjacent blade 13 to pass therethrough and into the inner lumen 17. FIGS. 2C and 2D are bottom perspectives view of the distal end 14 of the cutting element 12 showing a threaded opening 21 and inner lumen 17. The threaded opening 21 may be sized and configured to allow the insertion and removal of the extraction element 22 shown in FIG. 3. The cutting element 12 may be disposable, that is, a part of the device 10 replaced for each procedure.

Figure 3:
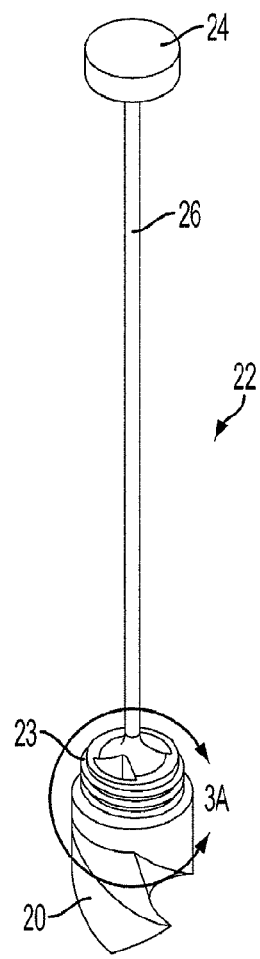
FIG. 3 is a top perspective view of an extraction element of the minimally-invasive device for bone graft harvesting of FIG. 1 according to an embodiment of the invention.
Figure 3A:
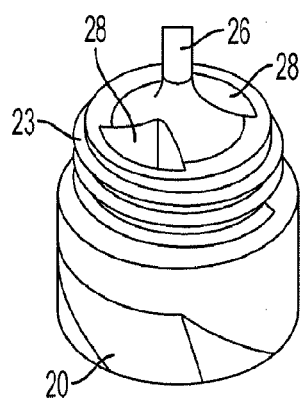
FIG. 3A is a detailed top perspective view of a distal end of the extraction element shown in FIG. 3.
Figure 3B:
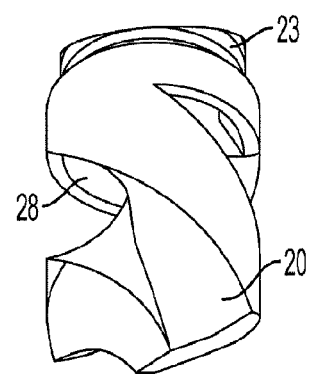
FIG. 3B is a detailed bottom perspective view of the distal end of the extraction element shown in FIGS. 3 and 3A.

FIG. 3 is a top perspective view of the extraction element 22 according to an embodiment of the invention. The extraction element 22 may be removably received within the inner lumen 17 of the hollow cutting element 12 to allow withdrawal of the bone material in the inner lumen 17. The extraction element 22 includes the cutting tip 20 provided at a distal end and spaced from a disk 24 provided at a proximal end. The cutting tip 20 and the disk 24 are coupled by an elongated rod 26. When disposed within the inner lumen 17 of the cutting element 12, an externally threaded portion 23 adjacent to the cutting tip 20 engages the threaded opening 21 to removably secure the extraction element 22 within the cutting element 12. The elongated rod 26 and disk 24 extend within the lumen 17 toward the proximal end of the cutting element 12. As shown in the detailed top and bottom perspective views of the distal end of the extraction element 22 depicted in FIGS. 3A and 3B, the cutting tip 20 may optionally include one or more openings 28 to allow cancellous bone material cut or morselized by the tip 20 to pass therethrough and into the inner lumen 17.

Figure 4:
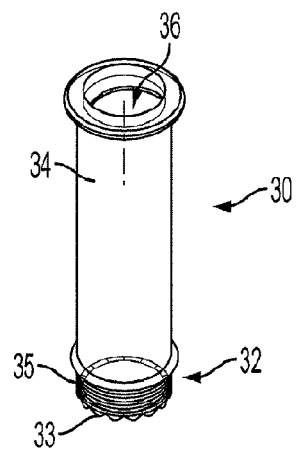
FIG. 4 is a perspective view of a tubular access port for use with the minimally-invasive device for bone graft harvesting of FIG. 1 according to an embodiment of the invention.
Figure 5:
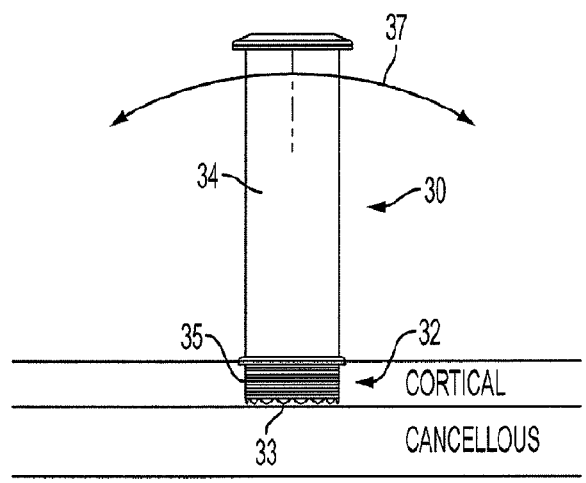
FIG. 5 is an illustrative side view of the tubular access port of FIG. 4 shown as being secured to a cortical shell or layer of a bone from which the graft is to be harvested.

FIG. 4 is a perspective view of a tubular access port 30 for use with the minimally-invasive bone graft harvesting device 10 according to an embodiment of the invention. The access port (trocar) 30 may be removably secured to a bone and allow passage of the hollow cutting element 12 therethrough to provide entry into cancellous bone with minimal disturbance of any non-osseous tissue. In the depicted embodiment, the access port includes a bone-engaging portion 32 and a flexible tube portion 34. The bone-engaging portion 32 includes a plurality of teeth 33 or serrations circumferentially arranged at a distal end of the access port 30 for cutting into a cortical shell or layer of the bone and further includes a threaded portion 35 for securing the access port 30 to the bone (see FIG. 5). The flexible tube portion 34 extends from the bone-engaging portion 32 to an opening 36 at a proximal end of the access port 30. The bone-engaging portion 32 may be formed of a rigid metal, plastic, or composite material. The flexible tube portion 34 may be formed of a softer, more flexible material such as a polymer, rubber, or the like and may be sufficiently flexible to bend laterally as indicated by arrow 37. According to an embodiment, the flexible tube portion 34 could be directly fixed to the bone-engaging portion 32 or, alternatively, could be coupled thereto by a ball-and-socket joint (not shown) to enhance the ability of the tube portion 34 to articulate relative to the bone-engaging portion 32. The access port 30 may allow a surgeon to insert the cutting element 12 therethrough to a predetermined depth in the cancellous bone and then use the access port 30 as a pivot point while the cutting element 12 is swept along an arc within the cancellous bone as described in further detail below. A stop or ridge (not shown) may extend from the outer surface of the cutting element 12 to provide an easy and repeatable way to fix the depth of insertion into the cancellous region.

Figure 6:
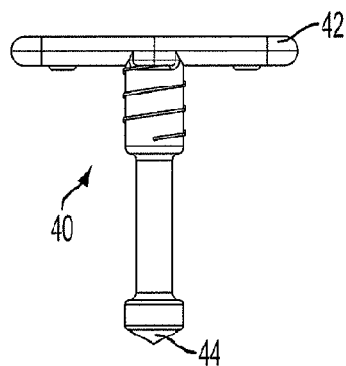
FIG. 6 is a side view of a tool for use with the access port of FIGS. 4 and 5 to create an open entry point through the cortical shell of the bone.
Figure 7:
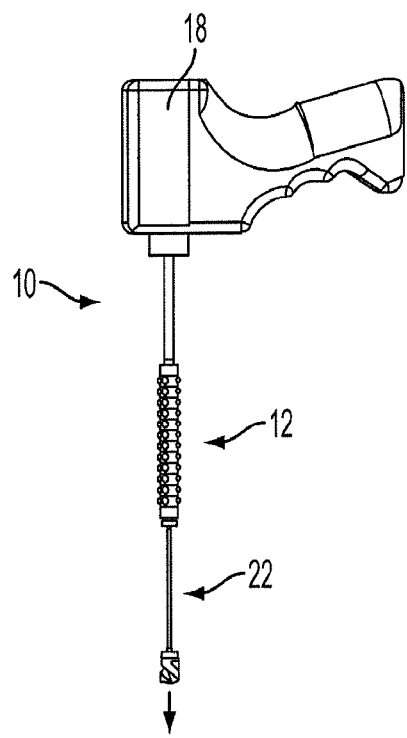
FIG. 7 is a side view of the minimally-invasive device for bone graft harvesting of FIG. 1 illustrating removal of the extraction element of FIG. 3 from within the hollow cutting element of FIG. 2.

FIG. 6 is a side view of a puncture tool 40 for use with the access port 30 to create an opening or entry point through the cortical shell of the bone to be harvested. For example, once the access port 30 has been inserted and secured to the cortical shell of the bone (e.g., the pelvic iliac crest), the puncture tool 40 may be inserted through opening 36 in the access port 30. By manually rotating the handle 42 the distal tip 44 may operate to remove the cortical shell within the diameter of the access port 30. Alternatively, the tool 40 may be used to screw the bone-engaging portion 32 of the access port 30 into the cortical shell while simultaneously removing a cylindrical volume of the cortical bone. Once the entry point is created, the tool 40 may be removed and the cutting element 12 of the device 10 may be inserted through the access port 30 to begin harvesting the cancellous region of the bone according to one of the harvesting procedures shown and described further below. Once a desired amount of bone material is cut and received within the cutting element 12, extraction of the material is necessary. FIG. 7, for example, depicts a side view of the minimally-invasive bone graft harvesting device 10 illustrating removal of the extraction element 22 from the distal end 14 of the hollow cutting element 12 to draw out cut cancellous bone material received within the inner lumen 17. Thus, the cutting element 12 and extraction element 22 can be assembled and disassembled as needed to allow the bone material to be collected.

Figure 8:
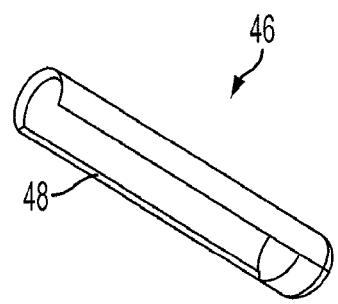
FIG. 8 is a perspective view of a safety cover for the cutting element of the minimally-invasive device for bone graft harvesting of FIG. 1 according to an embodiment of the invention.
Figure 9:
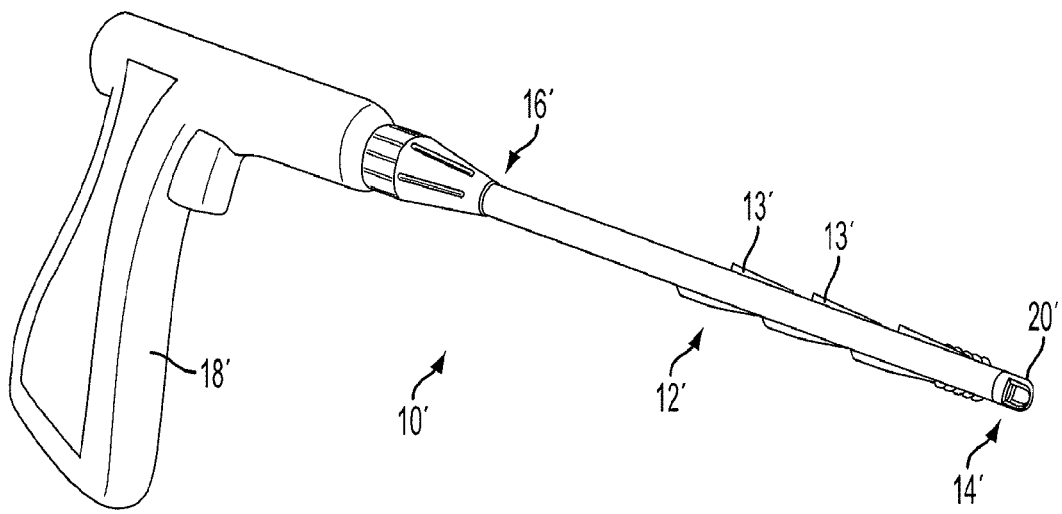
FIG. 9 is a perspective view of a minimally-invasive device for bone graft harvesting according to another embodiment of the invention.

FIG. 8 is a perspective view of an optional safety cover 46 for the cutting element 12 according to an embodiment of the invention. The optional cover 46 (see also FIGS. 1 and 1A) may be sized and configured to at least partially surround the cutting element 12 to provide a guard against cutting the cortical shell after insertion of the cutting element 12 into the cancellous region to be harvested. A portion 48 of the cover 46 may be open to allow the blades 13 of the cutting element 12 to cut bone material.

FIGS. 9-12 depict another embodiment of the minimally-invasive device 10' for bone graft harvesting. Similar to the device 10 depicted in FIGS. 1 and 1A, the device 10' includes a hollow cutting element 12' having a distal end 14' and a proximal end 16'. The proximal end 16' may be coupled to a powered or manually-operable rotary tool 18' such as, for example but not limited to, any currently available or specially designed surgical drill, power saw, or a manually gripped T-handle or knob. The device 10' may include a distal cutting tip 20' arranged at the distal end of the cutting element 12'. The cutting tip 20' may be part of an extraction element 22' (see FIG. 11) removably received within the cutting element 12'. The cutting element 12' may also include one or more blades 13' protruding from an outer surface 15' of the cutting element 12'.

Figure 10:
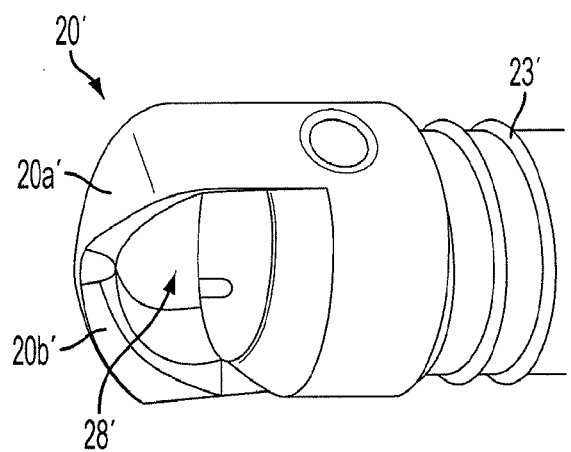
FIG. 10 is a detailed perspective view of a cutting tip disposed at a distal end of the cutting element of the minimally-invasive device for bone graft harvesting of FIG. 9.
Figure 11:
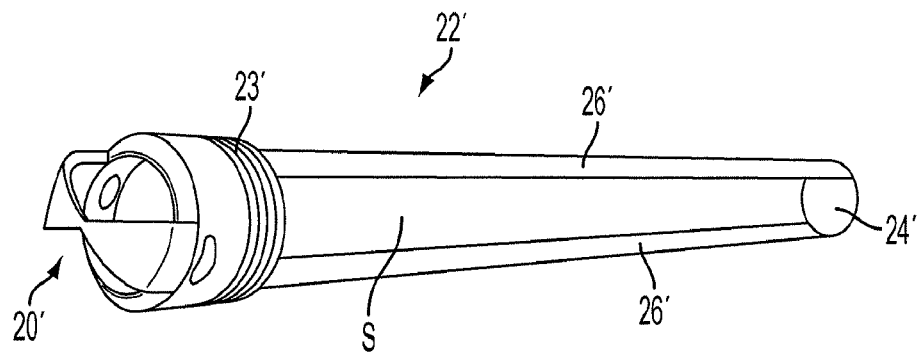
FIG. 11 is a perspective view of the extraction element of the minimally-invasive device for bone graft harvesting of FIG. 9.
Figure 12:
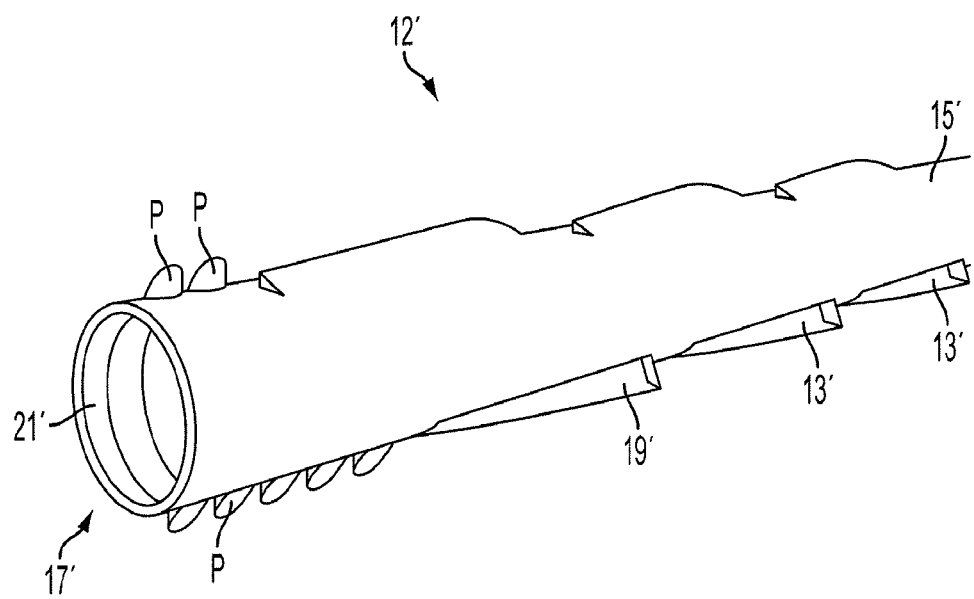
FIG. 12 is a perspective view of the distal end of the hollow cutting element of the minimally-invasive device for bone graft harvesting of FIG. 9.

FIG. 10 is a detailed perspective view of the cutting tip 20' disposed at a distal end of the extraction element 22'. The cutting tip 20' includes at least one fluted blade, such as, for example, two blades 20a', 20b' which facilitate the advancement of the device 10' forward through the cancellous bone region when rotated by the rotary tool 18'. Furthermore, the blades 20a', 20b' are radially inwardly arched to prevent perforation of an oppositely situated cortical shell during axial insertion of the cutting element 12'. The cutting tip 20' may also optionally include one or more openings 28' to allow cancellous bone material cut or morselized by the tip 20' to pass therethrough and into the inner lumen 17' of the cutting element 12'. An externally threaded portion 23' adjacent to the cutting tip 20' may be configured to engage the threaded opening 21' to removably secure the extraction element 22' within the cutting element 12'. FIG. 11 is a perspective view of the modified extraction element 22'. FIG. 12 is a perspective view of the modified hollow cutting element 12' similar to that described above and shown in FIGS. 2 and 2A-D but also including blades 13' of different size, shape, and angle relative to the longitudinal axis as well as a plurality of studs P or another textured or structured surface feature arranged near the distal end 14' to facilitate a sweeping movement of the device 10' along an arched path as described in further detail below.

Figure 13:
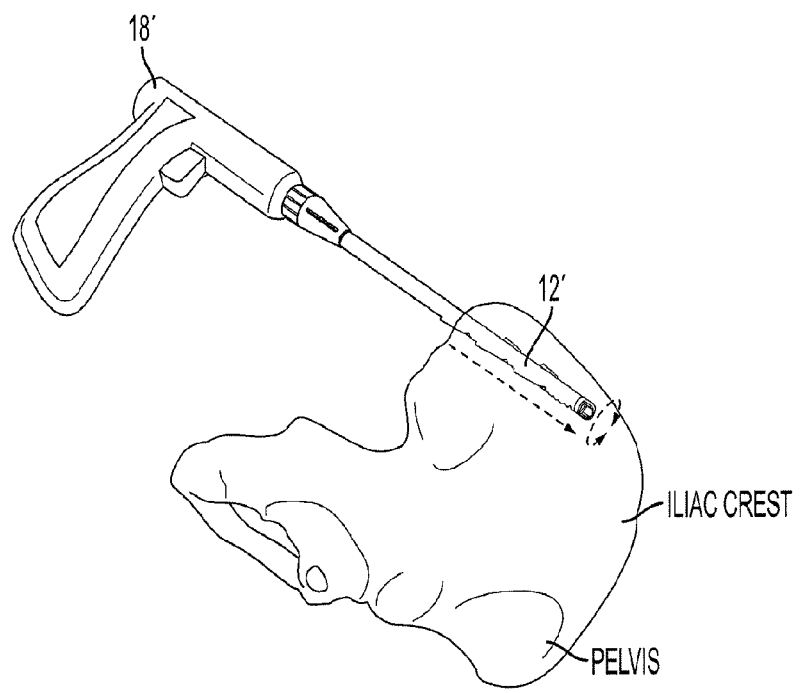
FIGS. 13 and 14 are illustrative perspective views of a method of using the minimally-invasive device for bone graft harvesting of FIG. 9 according to an embodiment of the invention.
Figure 14:
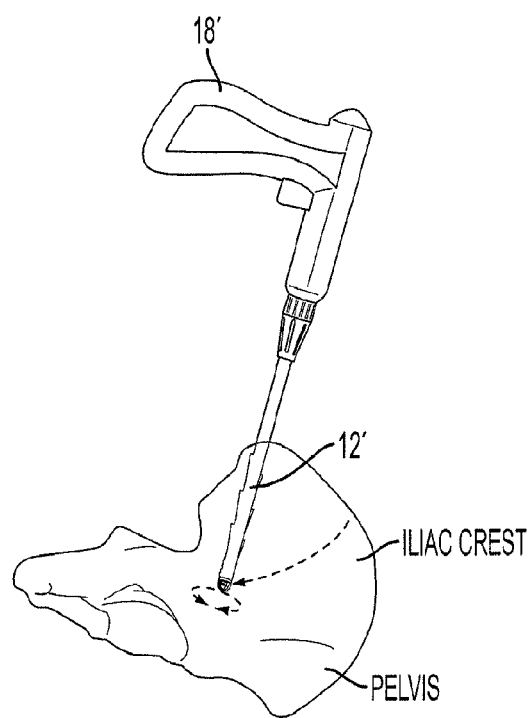

FIGS. 13 and 14 are illustrative perspective views of a method of using the minimally-invasive device 10 or 10' according to an embodiment of the invention. The method depicted is for harvesting bone material from the iliac crest of the pelvis, but the method is not limited to this particular bone and may be utilized for harvesting material from other bones, modified as necessary. After installation of the access port 30 (not shown in FIGS. 13 and 14), a guide wire (also not shown) may optionally be inserted by the surgeon using, for example, a Jamshidi needle or the like, in order to guide the trajectory of the cutting element 12' during axial (linear) insertion. The rotary tool 18' is then used to rotate the cutting element 12' during axial insertion as shown in FIG. 13. Once the distal end 14' of the cutting element 12' reaches a predetermined depth determined by the surgeon, the surgeon then moves the rotary tool 18' laterally thereby effectively pivoting the device 10' at the entry point and sweeping the distal end 14' of the cutting element 12' in an arc as shown in FIG. 14. The cutting element 12' continues to rotate during the sweeping motion. The surgeon may continue to sweep the device 10' until a sufficient amount of bone material is collected in the cutting element 12'. The surgeon may then withdraw the device 10' from the bone and remove the extraction element 22' from the distal end 14' of the cutting element 12' so that the disk 24' removes any cut cancellous bone material contained in the lumen 17' of the cutting element 12'.

Figure 15:
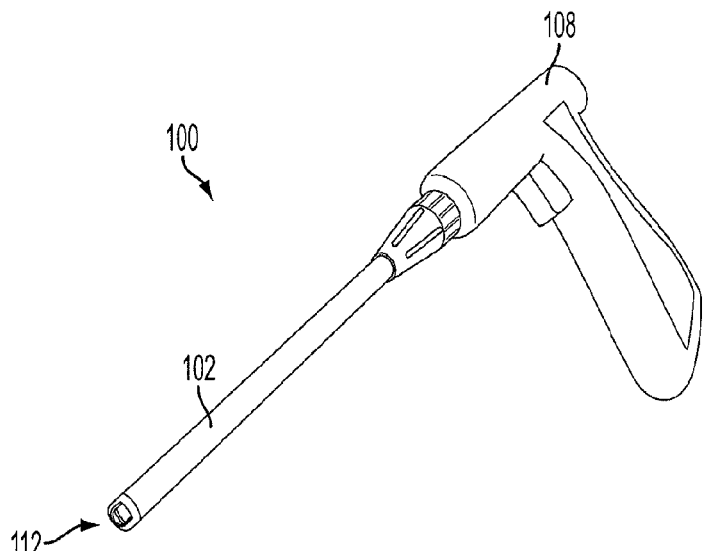
FIG. 15 is a perspective view of a minimally-invasive device for bone graft harvesting having a flexible hollow cutting element according to another embodiment of the invention.
Figure 16:
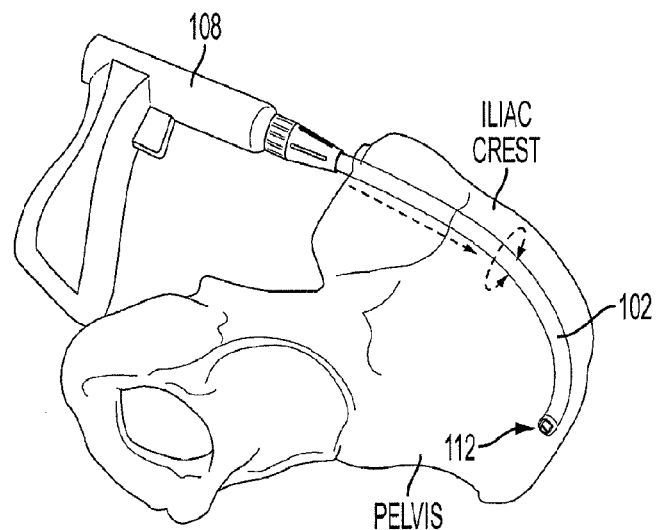
FIG. 16 is an illustrative perspective view of a method of using the minimally-invasive device of FIG. 15 according to another embodiment of the invention.
Figure 17:
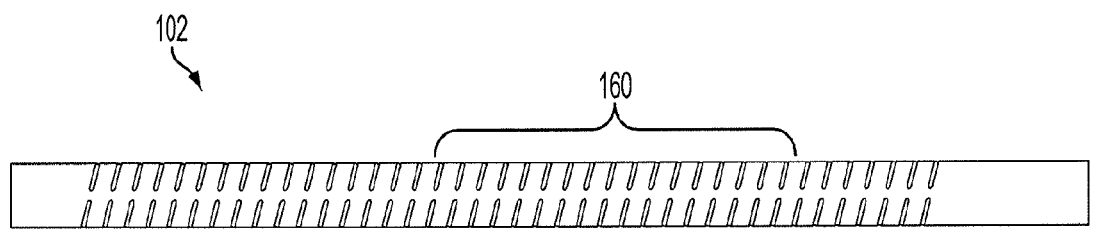
FIG. 17 is a schematic side view of the flexible hollow cutting element of FIG. 15 according to an embodiment of the invention.

FIG. 15 is a perspective view of another embodiment of the minimally-invasive device 100 for bone graft harvesting. In contrast with the devices described above, the device 100 includes a flexible hollow cutting element 102 and flexible extraction element (not shown) but otherwise similar to the aforementioned devices. According to the method depicted in FIG. 16, the cutting element 102 is coupled to the rotary tool 108 such as, for example, a standard surgical drill or T-handle, for rotational actuation. The cutting element 102 is inserted axially through an entry point (e.g., access port 30, not shown in FIG. 15). During axial insertion of the device 100, with or without a guide wire, the flexible cutting element 102 conforms to the natural curvature of the cancellous region within the cortical shell of the bone being harvested. As the cutting element 102 is rotated by the rotary tool 108 and simultaneously advanced forward axially, the dome shape of the cutting tip 112 (similar to cutting tip 20' shown in FIGS. 10 and 11) prevents the tip 112 from perforating through cortical bone and instead glides along the cortical boundary. The flexibility of the cutting element 102 is attributed to the material of the cutting element 102 and/or the design of certain notch patterns 160 cut into outer surface of the cutting element 102 as shown in FIG. 17.

Figure 18:
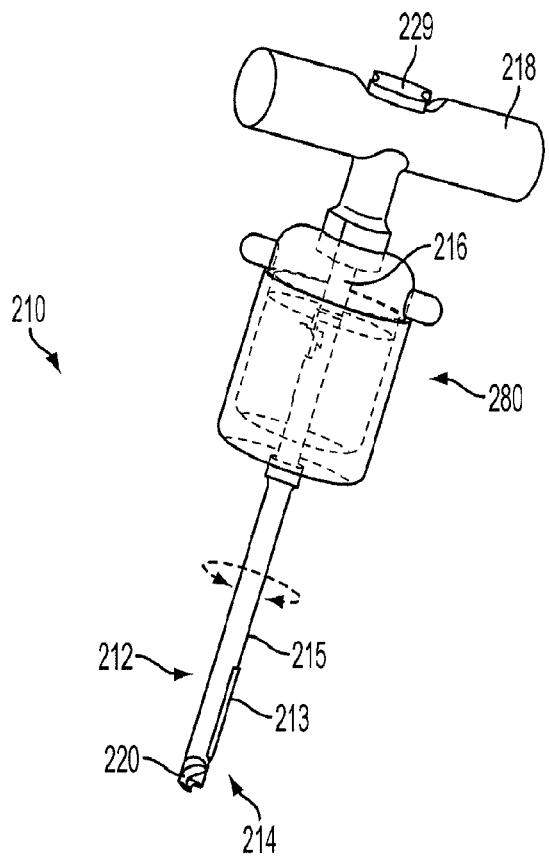
FIG. 18 is a perspective view of a minimally-invasive device for bone graft harvesting having a bone material collection canister according to another embodiment of the invention.
Figure 19:
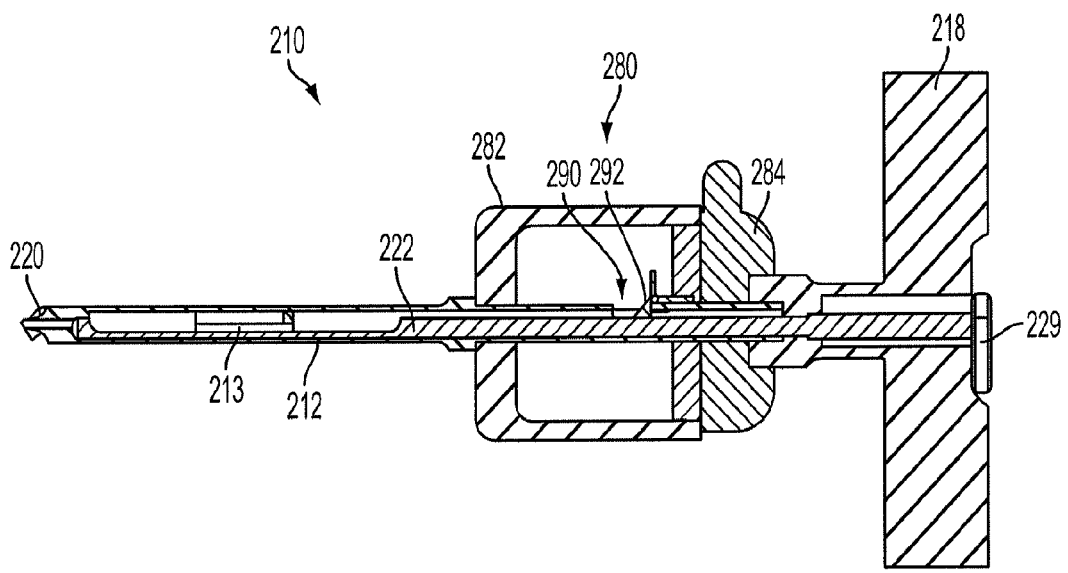
FIG. 19 is a side view of the minimally-invasive device for bone graft harvesting of FIG. 18.

FIGS. 18 and 19 are perspective and side views of a minimally-invasive device 210 for bone graft harvesting according to another embodiment of the invention. The device 210 may include a hollow cutting element 212 having a distal end 214 and a proximal end 216 and may be utilized according to any of the harvesting methods described herein (e.g., the sweeping technique). The proximal end 216 may be coupled to a powered or manually-operable rotary tool 218 such as, for example but not limited to, any currently available or specially designed surgical drill, power saw, or a manually gripped T-handle or knob. The T-handle 218 may contain a ratcheting mechanism to allow for continuous rotation of the handle without the need to periodically reposition the user's hand on the handle. The device 210 may include a distal cutting tip 220 arranged at the distal end of the cutting element 212. As shown, the cutting tip 220 is part of the cutting element 212. As in the previously described embodiments, the cutting element 212 may also include one or more blades 213 protruding from an outer surface 215 of the cutting element 212, each blade 213 having an opening arranged adjacent thereto to allow cancellous bone material cut or morselized by the adjacent blade 213 to pass therethrough and into the inner lumen 217 of the cutting element 212. The extraction element 222 may be removably received within the inner lumen 217 of the hollow cutting element 212 to allow withdrawal of cut bone material received in the inner lumen 217. In contrast with the foregoing embodiments, the extraction element 222 may be configured to be moved or at least partially withdrawn through the proximal end of the cutting element 212. The extraction element 222 includes a disk 224 at a distal end spaced from a manually grippable portion 229 arranged at the proximal end. The distally arranged disk 224 is coupled to the proximal end by an elongated rod including, for example, at least one elongated leg 226 defining an open area such as, for example, a slot for receiving the cut bone material. The device 210 also include a bone material collection canister 280 coupled to the proximal end of the cutting element 212 for receiving cut bone material from the inner lumen 217 of the cutting element 212 each time the extraction element 222 is retracted in the proximal direction.

As shown in FIG. 19, the canister 280 may include a lower portion 282 and an upper portion 284 coupled together to define an interior storage volume. The lower and upper portions 282, 284 may be removably coupled together by a threaded, snap-fit, and/or friction-fit connection to allow access to the interior storage volume for removal of the harvested bone material. The cutting element 212 may include a portion extending through the interior storage volume and having a port or window 290 in the outer surface of the cutting element 212 to allow cut bone material to pass from within the inner lumen 217 into the canister 280 upon axial movement of the extraction element 222 in the proximal direction. A retractable deflection element 292 in the form of a ramp may be provided to extend through the window 290 into the inner lumen 217 to assist with removal of the cut bone material into the canister 280 when the extraction element 222 is moved proximally. The deflection element 292 may be movable or pivotable between a first position (not shown), in which the extraction element 222 is extended fully in the distal direction and blocks entry of the deflection element 292 into the window 290, and a second position in which the extraction element 222 is extended fully in the proximal direction and allows entry of the deflection element 292 through the window 290. The deflection element 292 may be spring-biased toward the second position.

Figure 20:
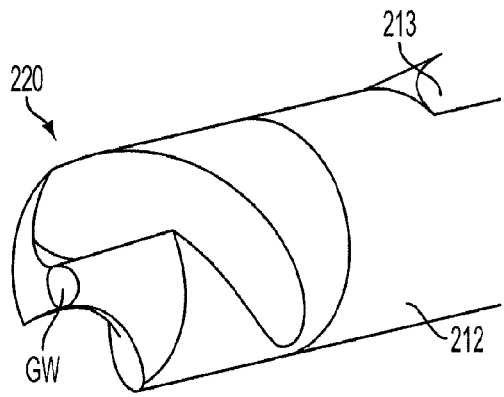
FIG. 20 is a perspective view of the cutting tip provided at the distal end of the cutting element of the minimally-invasive device for bone graft harvesting of FIG. 18.

FIG. 20 is a perspective view of the cutting tip 220 provided at the distal end 214 of the cutting element 212. As shown in FIG. 20, a central hole GW may be provided in order to allow the device 210 to be passed over a guide wire (not shown) during insertion into the bone being harvested for the bone graft.

Figure 21:
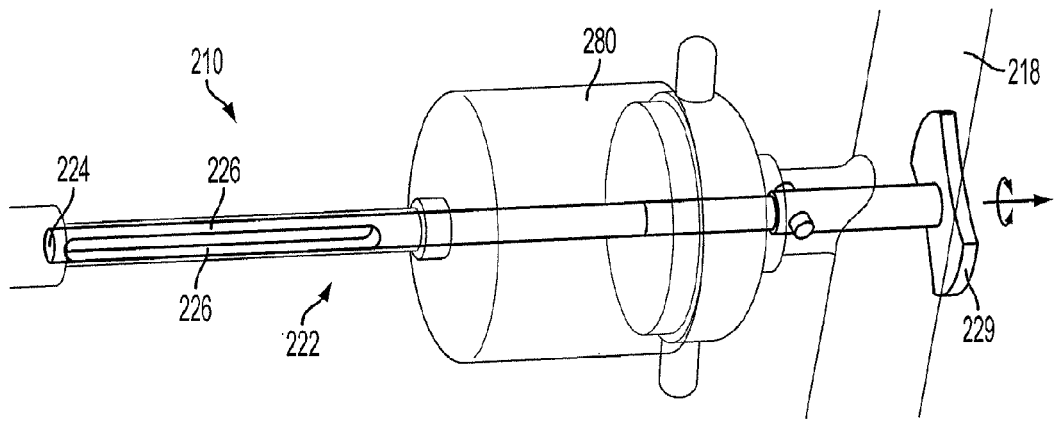
FIG. 21 is a perspective view of the extraction element of the minimally-invasive device for bone graft harvesting of FIG. 18.
Figure 22:
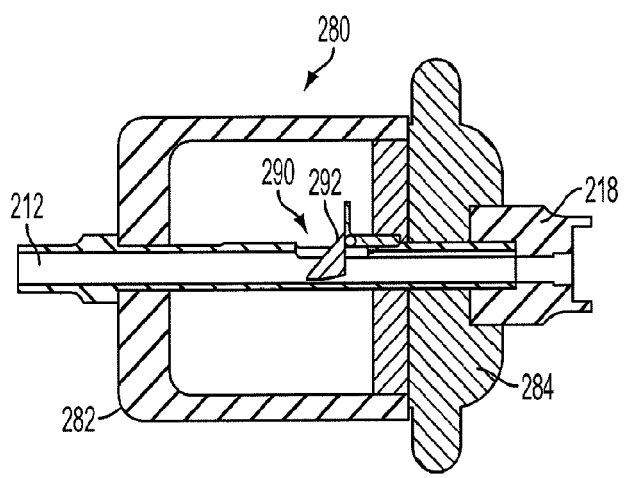
FIG. 22 is a perspective view of the bone material collection canister of the minimally-invasive device for bone graft harvesting of FIG. 18, including a deflection element arranged to cooperate with the extraction element to remove bone material from the extraction element.

FIGS. 21 and 22 depict perspective views of the device 210 including operation of the extraction element 222 to remove cut bone material from the inner lumen 217 of the cutting element 212 and deposit the same in the canister 280. During removal of the cut or morselized bone material, the extraction element 222 may be manually rotated approximately 90 degrees using the grippable knob 229 provided at the proximal end adjacent to the T-handle 218. In this rotated position, the legs 226 of the extraction element 222 may cover the adjacent openings of the blades 213 on the outer surface of the cutting element 212 and functionally block further bone material from entering or exiting the lumen 217 of the cutting element 212. Once in the rotated position, the extraction element 222 can be moved axially in the proximal direction through the lumen 217 of the cutting element 212. As the disk 224 of the extraction element 222 pulls the bone material up the lumen 217 of the cutting element 212, the bone material provided between the legs 226 approaches the window 290 provided in the outer face of the cutting element 212 within the canister 280. The deflection element 292 enters the lumen 217 through the window 290 and provides a ramp to guide the bone material out of the lumen 217 and into the interior storage volume of the canister 280. Once the bone material is removed from the lumen 217 of the cutting element 212, the user may release the proximal knob 229, which may cause the extraction element 222 to automatically return to its initial distally extended position, e.g., through a spring-loaded mechanism (not shown). The canister 280 may be graduated in order to indicate a volume of the bone graft collected therein. The canister 280 can be opened for facile removal of the material. The canister may also include an ergonomic hand placement for the user to ensure easy maneuverability of the device 210.

Embodiments of the device may also include a sensing element (not shown) that allows for safer operation by detecting when the distal tip of the cutting element reaches a boundary between the cancellous and cortical region inside the bone from which the graft is being harvested (e.g., iliac crest of the pelvis) to avoid penetration of the cortical shell and possible resulting damage to vascular and nervous tissue. For example, the sensing element may be configured to detect the change in density at the cortical/cancellous boundary and may transmit a signal (e.g., wired or wirelessly) to a receiver in the powered rotary tool which automatically stops rotation of the cutting element. Alternatively or concurrently, the sensing element may be configured to alert or notify the user (e.g., surgeon) before perforation of the cortical layer occurs, for example, by activating a light, sound, alarm or other notification device. The sensing element may utilize known electrical and/or mechanical elements, sensors (e.g., ultrasonic probes), tactile feel or a combination thereof to detect the boundary, stop the cutting element, and/or alert the user.

Application of the device can be extended from use in the iliac crest to other anatomical regions of the body (e.g., jaw, femur, tibia) where bone graft is often collected for various uses. The geometries and dimensions of the device may or may not have to be altered to fit the new anatomical space, and components may or may not have to be added to or removed from the system to maintain intended functionality in these applications.

Surgical Method Example 1

Iliac Crest Bone Harvesting—Proximal Pivot

The surgeon makes a small opening in the posterior superior iliac spine (PSIS) using an awl or rongeur. An access port is hammered, screwed, or otherwise inserted and secured into the PSIS. A blunt-tipped guide wire may optionally be inserted through the opening in the PSIS using a Jamshidi needle or the like, and is passed down to the anterior superior iliac spine (ASIS). The surgeon may then pass the device over the guide wire while powering it with either a surgical drill or a T-handle. When the distal end of the device has reached the ASIS, the surgeon may remove the guide wire and sweep the distal aspect of the device (while continuing to turn the drill) about a proximal pivot point laterally. The surgeon can then remove the device and extract the collected bone graft from the lumen.

Surgical Method Example 2

Iliac Crest Bone Harvesting—Distal Pivot

The device can be swept using a distal pivot. For this method, the distal end is fixed and the proximal end of the device is swept along the iliac crest near the PSIS in an arc. According to the method, the surgeon makes a small opening in the PSIS using an awl or rongeur. A blunt-tipped guide wire may optionally be inserted through the opening in the PSIS and is passed down to the ASIS. The surgeon may then pass the device over the guide wire while powering it with either a surgical drill or a T-handle. When the distal end of the device has reached the ASIS, the surgeon sweeps the drill or T-handle laterally while the cutting element is pivoted at the distal tip residing inside the cancellous region of the iliac crest. The surgeon can then remove the device and extract the collected bone graft from the lumen or collection container.

Surgical Method Example 3

Iliac Crest Bone Harvesting—Flexible Cutting Element

The surgeon makes a small opening in the PSIS using an awl or rongeur. A blunt-tipped guidewire may optionally be inserted through the opening in the PSIS and is passed down to the ASIS. The surgeon may pass the device over the guide wire until it reaches the ASIS. The surgeon may then extract the device and guide wire and insert the device along a new trajectory from the PSIS to collect a different region of bone. The surgeon will then plunge out the collected bone from within the lumen of the flexible cutting element and/or the collection container.

Surgical Method Example 4

Sacrum Bone Harvesting—Flexible Cutting Element

The surgeon makes a small incision above the sacrum. A blunt-tipped guide wire may optionally be inserted through the opening in the sacrum and is passed into the pelvic bone. The surgeon may pass the device over the guide wire until it reaches the end of the guide wire. The surgeon may then extract the device and insert it along a new trajectory from the sacrum to extract a different region of bone. The surgeon will then plunge out the collected bone from within the lumen of the flexible shaft and/or the collection container The embodiments illustrated and discussed in this specification are intended only to teach those skilled in the how to make and use the invention. In describing embodiments of the invention, specific terminology is employed for the sake of clarity. However, the invention is not intended to be limited to the specific terminology so selected. The above-described embodiments of the invention may be modified or varied, without departing from the invention, as appreciated by those skilled in the art in light of the above teachings. It is therefore to be understood that, within the scope of the claims and their equivalents, the invention may be practiced otherwise than as specifically described.

We claim:

1. A minimally-invasive bone graft harvesting device, comprising:
   a hollow cutting element defining a longitudinal axis and including:
   a distal end;
   a proximal end adapted to be coupled to a powered or manual-operated rotary tool;
   an inner lumen extending longitudinally between the distal and proximal ends; and
   one or more blades protruding from an outer surface of the cutting element, wherein each blade is arranged adjacent to an opening extending between the outer surface and the inner lumen to allow cancellous bone material cut by each blade to pass through the opening into the inner lumen;
   an extraction element within the inner lumen of the hollow cutting element to allow withdrawal of the bone material in the inner lumen;
   a bone material collection canister, wherein the cutting element extends through the canister; and
   a deflection element arranged within the canister and adjacent to a hole in the outer surface of the cutting element to remove cut bone material from within the inner lumen when the extraction element is moved proximally.

2. The minimally-invasive bone graft harvesting device according to claim 1, wherein the cutting element includes a cutting tip disposed at the distal end.

3. The minimally-invasive bone graft harvesting device according to claim 2, wherein the extraction element is movable through an opening at the proximal end of the cutting element.

4. The minimally-invasive bone graft harvesting device according to claim 3, wherein the extraction element includes a distal disk and a proximal handle spaced from one another and coupled together by at least one elongated rod extending parallel to the longitudinal axis.

5. The minimally-invasive bone graft harvesting device according to claim 4, wherein the at least one elongated rod comprises one or more legs arranged to define an open area to receive the cut bone material passed into the inner lumen.

6. The minimally-invasive bone graft harvesting device according to claim 4,
   wherein the cutting element includes a hole in the outer surface along a portion enclosed within the canister, whereby when the extraction element is moved longitudinally toward the proximal end of the cutting element, bone material disposed within the inner lumen is moved proximally by the distal disk and deposited in the collection canister through the hole in the outer surface of the cutting element.

7. The minimally-invasive bone graft harvesting device according to claim 1, wherein the cutting element and the extraction element include a continuous through hole along the longitudinal axis to receive a guide wire.

8. A minimally-invasive bone graft harvesting device, comprising:
   a hollow cutting element defining a longitudinal axis and including:
   a distal end having a cutting tip;
   a proximal end coupled to a powered or manual-operated rotary tool;
   an inner lumen extending longitudinally between the distal and proximal ends; and
   at least one opening extending between an outer surface of the cutting element and the inner lumen to allow cancellous bone material to pass through the opening into the inner lumen;
   an extraction element movably received within the inner lumen of the hollow cutting element to allow withdrawal of the bone material in the inner lumen, wherein the extraction element extends through an opening at the proximal end of the cutting element;
   a bone material collection canister, wherein the cutting element extends through the canister and includes a hole in the outer surface along a portion enclosed within the canister, whereby when the extraction element is moved longitudinally toward the proximal end of the cutting element, bone material disposed within the inner lumen is moved proximally by a distal disk and deposited in the bone material collection canister through the hole in the outer surface of the cutting element; and
   a deflection element arranged within the canister and adjacent to the hole in the outer surface of the cutting element to remove cut bone material from within the inner lumen when the extraction element is moved proximally.

9. The minimally-invasive bone graft harvesting device according to claim 8, wherein the extraction element includes a distal disk and a proximal handle spaced from one another and coupled together by at least one elongated rod extending parallel to the longitudinal axis.

* * * * *